US012408643B2

(12) United States Patent
Yoshioka et al.

(10) Patent No.: US 12,408,643 B2
(45) Date of Patent: *Sep. 9, 2025

(54) APPARATUS FOR PRODUCING A BAGWORM SILK THREAD, AND METHOD OF PRODUCING LONG BAGWORM SILK THREAD

(71) Applicants: NATIONAL AGRICULTURE AND FOOD RESEARCH ORGANIZATION, Tsukuba (JP); KOWA COMPANY, LTD., Nagoya (JP)

(72) Inventors: Taiyo Yoshioka, Tsukuba (JP); Tsunenori Kameda, Tsukuba (JP); Takahiro Kitamura, Tsukuba (JP); Akimune Asanuma, Tsukuba (JP)

(73) Assignees: NATIONAL AGRICULTURE AND FOOD RESEARCH ORGANIZATION, Tsukuba (JP); KOWA COMPANY, LTD., Nagoya (JP)

( * ) Notice: Subject to any disclaimer, the term of this patent is extended or adjusted under 35 U.S.C. 154(b) by 17 days.

This patent is subject to a terminal disclaimer.

(21) Appl. No.: 18/297,360

(22) Filed: Apr. 7, 2023

(65) Prior Publication Data

US 2023/0240274 A1     Aug. 3, 2023

Related U.S. Application Data

(62) Division of application No. 17/299,360, filed as application No. PCT/JP2019/047403 on Dec. 4, 2019, now Pat. No. 11,877,567.

(30) Foreign Application Priority Data

Dec. 4, 2018 (JP) ................. 2018-227669

(51) Int. Cl.
  A01K 67/35     (2025.01)
  D01B 7/00      (2006.01)
  D01B 7/04      (2006.01)

(52) U.S. Cl.
  CPC ............... *A01K 67/35* (2025.01); *D01B 7/00* (2013.01); *D01B 7/04* (2013.01)

(58) Field of Classification Search
  CPC . D01B 7/00; D01B 7/04; A01K 67/04; A01K 67/033
  See application file for complete search history.

(56) References Cited

U.S. PATENT DOCUMENTS 1,412,011 A   4/1922  Bohm
1,577,118 A   3/1926  Fioruzzi
(Continued)

FOREIGN PATENT DOCUMENTS

CN    1608489 A    4/2005
CN    102677182 A  9/2012
(Continued)

OTHER PUBLICATIONS

Osaki, "Animals Teach Science on Natural Fibers:—Spider's Silks, Bagworm's Silks, and Collagen Fibers—", Journal of the Society of Fiber Science and Technology, 2002, vol. 58, No. 3, pp. 74-78, Partial English Translation 3 pages.
(Continued)

*Primary Examiner* — Aiying Zhao
(74) *Attorney, Agent, or Firm* — Lucas & Mercanti, LLP

(57) ABSTRACT

Disclosed is a method of efficiently producing a long bagworm silk thread containing no contaminant while preventing a change in the spinning direction and the runaway of the bagworm from a rail, and alleviating a burden on the bagworm; and an apparatus for implementing the thread-producing method. Provided is an apparatus for producing a
(Continued)

bagworm silk thread, having a movable rail having a width smaller than the maximum width between the right and left legs of a bagworm and configured to move in the longitudinal direction and to be able to hold with the legs of the bagworm; and a fixator configured to fix a bagworm, wherein the fixator is placed at a position such that the fixed bagworm can hold the movable rail.

5 Claims, 10 Drawing Sheets

(56) References Cited

U.S. PATENT DOCUMENTS

| | | | |
|---|---|---|---|
| 3,994,259 A | | 11/1976 | Sakamura |
| 4,063,285 A | | 12/1977 | Nagaoka |
| 6,412,261 B1 | * | 7/2002 | Welshans ............... D01B 7/00 57/3 |
| 2006/0162313 A1 | * | 7/2006 | Shimizu ............... D01B 7/04 57/243 |
| 2013/0281668 A1 | * | 10/2013 | Vollrath ............... D01B 9/00 119/270 |
| 2018/0008750 A1 | * | 1/2018 | Kweon ............... A61F 2/02 |
| 2018/0264170 A1 | * | 9/2018 | Kweon ............... A61F 2/0063 |
| 2020/0157706 A1 | * | 5/2020 | Kameda ............... D01B 7/04 |
| 2020/0277710 A1 | * | 9/2020 | Yoshioka ............... A01K 67/04 |

FOREIGN PATENT DOCUMENTS

| | | | | |
|---|---|---|---|---|
| GB | 443886 A | | 3/1936 | |
| IN | 200377 A1 | | 7/2006 | |
| IN | 201731006396 A | | 4/2018 | |
| JP | 2004244762 A | | 9/2004 | |
| JP | 2018074951 A | | 5/2018 | |
| JP | 2018197415 A | | 12/2018 | |
| WO | WO-2005049899 A1 | * | 6/2005 | ............... D01B 7/00 |
| WO | 2012080510 A1 | | 6/2012 | |
| WO | 2012165477 A1 | | 12/2012 | |

OTHER PUBLICATIONS

Kuwana et al., "High-Toughness Silk Produced by a Transgenic Silkworm Expressing Spider (*Araneus ventricosus*) Dragline Silk Protein", PLOS ONE, 2014, vol. 9, Issue 8, e105325, pp. 1-11.

Gosline et al., "The Mechanical Design of Spider Silks: From Fibroin Sequence to Mechanical Function", The Journal of Experimental Biology, 1999, vol. 202, pp. 3295-3303.

Organic Gardening, YouTube Video: "How to keep birds, squirrels, other animals away from your fruit trees", Aug. 15, 2014, Retrieved from internet: https://www.youtube.com/watch?v=1kNf3FoP9Dc.

Office Action for Corresponding Indian Patent Application No. 202117029215, Mar. 16, 2023.

Zhang, "Study of the identification and Occurrence of Clania variegate Snellen", Journal of Anhui Agri Sci, 2010, vol. 38, No. 16, pp. 8499-8500, English Abstract.

Office Action for Corresponding Chinese Application No. 201980079655.3, Aug. 7, 2024, 6 pages.

* cited by examiner (a)

(b)

(c)

(a)

(b)

(a)

(b)

(c)

(d)

APPARATUS FOR PRODUCING A BAGWORM SILK THREAD, AND METHOD OF PRODUCING LONG BAGWORM SILK THREAD

CROSS-REFERENCE TO RELATED APPLICATIONS

This application is a Divisional Application of U.S. application Ser. No. 17/299,360, filed Jul. 1, 2021, which in turn is a 371 of PCT/JP2019/047403, filed Dec. 4, 2019, which claims the benefit of Japanese Patent Application No. 2018-227669, filed Dec. 4, 2018, the contents of each of which are incorporated herein by reference herein.

TECHNICAL FIELD

The present invention relates to a method of producing a bagworm silk thread, an apparatus for producing the thread using the method, and a method of producing a long bagworm silk thread.

BACKGROUND ART

The thread composed of an insect cocoon or a hair of mammal has been used as an animal fiber for a cloth and the like since long time ago. In particular, a silk thread from a silk moth (*Bombyx mori*) larva, namely a silkworm, which is herein often referred to as a "silkworm silk thread", has excellent properties for absorption and desorption of moisture, moisture retention, and heat retention, and also has a unique gloss and a smooth texture. Therefore, the silkworm silk thread is valuable and expensive natural material even today.

Recently, research is ongoing to search from nature for an animal fiber having properties comparable or superior to those of a silkworm silk thread and to utilize such an animal fiber as a novel natural material.

A thread from a spider (often referred to herein as a "spider thread") is one such material. A spider thread shows flexibility and elasticity and shows an elastic force several times greater than that of polystyrene. Because of this, a spider thread is expected to be used as a special material for a medical material for suture and emergency ropes, protective clothes, or the like (Non-Patent Literature 1 and 2). However, many problems remain to be solved before practical use of the spider thread. First, mass-production of spider threads is not feasible because mass-rearing of spiders and production of a large amount of thread from spiders are difficult, which also results in a problem of high production cost. This problem is now being solved by using a recombinant silkworm or *Escherichia coli* producing a spider thread (Patent Literature 1 and Non-Patent Literature 2). However, a recombinant is allowed to be reared or cultured only in facilities with specialized equipment, which raises a new problem, for example, with a large maintenance or management burden.

Now, an animal fiber having properties mechanically superior to those of a silkworm silk thread or a spider thread exists in nature. One such fiber is the thread spun by a bagworm (also known as "basket worm"; the thread is herein often referred to as "bagworm silk thread"). For example, a silk thread from the bagworm *Eumeta minuscula* has a very high strength, as indicated by the elastic modulus value which is 3.5 times higher than that of a silkworm silk thread and 2.5 times higher than that of a spider thread from *Nephila clavata* (Non-Patent Literature 1 and 3). Additionally, a bagworm silk monofiber has a cross-sectional area nearly one-seventh as large as that of a silkworm silk monofiber, which allows production of fine, thin and light fabrics with a smooth texture. Moreover, a bagworm silk thread has a gloss and a shiny appearance comparable or superior to that of a silkworm silk thread.

The bagworm is advantageous also in terms of management. For example, since the silkworm feeds on only raw leaves of mulberry in principle, the region for rearing and season for rearing depend on the supply area of mulberry leaves and the season of mulberry leaf development. In contrast, the bagworm is euryphagous, the specificity for food leaves is low, and many species of the bagworm can feed on leaves of trees of various species. Accordingly, food leaves for the bagworm are easily available, and the bagworm can be reared in any region. Also, the bagworm of some species can feed on leaves of evergreen trees. Thus, differently from mulberries, which are deciduous trees, it is possible to supply food leaves all year round. Moreover, the bagworm is smaller in size than the silkworm and requires a rearing space equal to or less than that required for rearing the silkworm, which makes mass rearing easy. Thus, the cost for rearing can significantly be reduced compared with that for rearing the silkworm. Additionally, bagworm silk threads can be directly obtained from wild-type bagworms. Therefore, production of recombinant bagworms and special maintenance and management equipment are not needed, differently from spider thread production.

As described above, the bagworm silk thread has properties superior to those of a conventional animal fiber and also has many advantages for their management and production, and thus, can become an extremely promising novel natural material.

However, there are some problems to be solved so that bagworm silk thread can be put to practical use. One of the problems is that it is difficult to obtain a long fiber from a bagworm required for the use as a long fiber. In the case of a silkworm, a cocoon is performed by continuous spinning, and a long fiber can thus be relatively easily obtained by silk cocoon degumming and reeling. In contrast, a bagworm pupates in its nest where the bagworm spends its life in the larval stage, and therefore spins no cocoon for pupation. Additionally, a nest of a bagworm is extended as the bagworm grows from the first instar in principle, and old and new silk threads are mixed together in the nest. Additionally, a nest of a bagworm has an opening at one end of the longitudinal axis, out of which the bagworm exposes its head and a portion of its thorax for migration and eating, and an outlet at the other end, through which excrement such as feces is discharged. It means that each bagworm nest always has two openings and the presence of the openings makes the silk thread in the nest be fragmented and to be discontinued. Because a bagworm nest is naturally assembled by relatively short silk threads entangled with each other, as described above, no long fiber more than 1 m usually exists in the nest. Additionally, by any existing technology, a thread can be spun only from a fiber in the innermost layer, which contains little gummy material adhered around a silk thread, and the silk thread obtained from the innermost layer is only less than 50 cm long.

For practical application of the bagworm silk thread, another problem is that pieces of leaves and twigs and the like are inevitably attached on the surface of a bagworm nest. These contaminants should be completely removed for commercialization of a bagworm silk thread. However, the removal operation requires enormous labor and cost, thus resulting in increased production cost. Additionally, complete removal of the contaminants is difficult with existing technologies, which leads to loss of quality of a final product due to, for example, contamination with a minute amount of small leaves as well as light-brown staining of a silk thread with pigments from the contaminants.

For the above-mentioned reasons, it has been almost impossible to obtain a meter-scale bagworm silk monofiber by the existing technology. Therefore, no fabric interwoven with a bagworm silk thread has been known. In fact, conventional products using a bagworm silk thread, such as purses or sandals, are just manufactured using unwoven fabrics, which are prepared by removing contaminants, such as pieces of leaves and twigs, from bagworm nests, expanding and then shaping the resulting bagworm nests to join the bagworm nests together as if to prepare a patchwork.

Accordingly, it has been essential to develop a method of producing a pure and long bagworm silk thread without contaminant, for practical application of a bagworm silk thread as a novel material of biological origin.

To solve the above-mentioned problems, the present inventors have vigorously made studies, and have consequently developed a method of collecting a foothold silk thread which a bagworm spins as a foothold onto leaves and twigs to prevent the bagworm from falling from the twigs and the like, in which the bagworm is caused to spin the foothold silk thread in longer size. This method utilizes the nature of a bagworm which continues to spin a foothold silk thread along the rail having a specific width, by placing the bagworm on the rail. The inventors have succeeded in using this method for stable mass-production of a meter-scale continuous pure bagworm silk thread, which has hitherto been considered impossible. Thus, on the basis of this method, the present inventors filed a patent application (Japanese Patent Application No. 2017-110003).

The above-mentioned method is epoch-making as a method of producing a long bagworm silk thread, but poses new problems concurrently. One of the problems is about the stamina of a bagworm. A bagworm spins a thread, holding a nest, and thus, needs the energy for supporting the nest in addition to the energy for spinning. Because of this, spinning for a long time in one thread-producing process creates an undue burden on a bagworm. Additionally, a bagworm placed on a rail spins a thread in a given direction of movement along the rail in principle, but the bagworm has a relatively high degree of freedom, and thus, the bagworm occasionally changes the direction of movement, or leaves the rail in some cases. Such a change in the direction of movement can cause the tangle and tear of the thread being collected. Furthermore, in bagworm silk threads layered on a loop-shaped rail, the cumulated silk threads are strongly cemented each other with a gummy material, and in some cases, this makes it difficult to collect the threads from the rail or to carry out degumming, that is, remove the gummy material.

CITATION LIST

Patent Literature

Patent Literature 1: WO2012/165477

Non-Patent Literature

Non-Patent Literature 1: Shigeyosi Ohsaki, 2002, Sen'i Gakkaishi (Sen'i To Kogyo), 58: 74-78.
Non-Patent Literature 2: Kuwana Y, et al., 2014, PLoS One, DOI: 10.1371/journal.pone.0105325

Non-Patent Literature 3: Gosline J. M., et al., 1999, 202, 3295-3303.

SUMMARY OF INVENTION

Technical Problem

An object of the present invention is to develop: a method of efficiently producing a long bagworm silk thread containing no contaminant in addition to preventing a change in the spinning direction and the runaway of the bagworm from the rail, and further to alleviating a burden on the bagworm; and an apparatus for implementing the thread-producing method.

Solution to Problem

The present inventors have made further studies to solve the above-mentioned new problems, and have consequently succeeded in developing such a method of producing a long bagworm silk thread as to solve the problems and an apparatus for implementing the method. Now, the newly developed producing method and thread-producing apparatus make it possible to automate the processes from the spinning of a bagworm silk thread through to the collection of the thread, and furthermore, enable the spinning process and the collection process to be performed concurrently. The present invention is based on the above-mentioned development results and will provide the following items.

(1) An apparatus for producing a bagworm silk thread, comprising:
   a movable rail configured to move in the longitudinal direction; and
   a fixator configured to fix a bagworm, wherein
   the movable rail has a width smaller than the maximum width between the right and left legs of the bagworm fixed to the fixator, and is configured to be able to hold with the legs of the bagworm, and
   the fixator is placed at a position such that the fixed bagworm can hold the movable rail.

(2) The apparatus for producing a bagworm silk thread according to (1), further comprising one or more peeling containers, wherein
   the peeling container is configured to store a peeling solution and/or vapor for peeling the spun bagworm silk thread from the movable rail, and
   a part of the movable rail is placed at a position such that the part can contact with the peeling solution and/or the vapor in the peeling container.

(3) The apparatus for producing a bagworm silk thread according to (2), further comprising a collection device, wherein the collection device is configured to collect the bagworm silk thread peeled from the movable rail.

(4) The apparatus for producing a bagworm silk thread according to (2) or (3), further comprising one or more thread hooks, wherein the thread hook is configured to change the thread reeling direction of the bagworm silk thread peeled from the movable rail.

(5) The apparatus for producing a bagworm silk thread according to any one of (1) to (4), wherein the movable rail is a loop-shaped rail.

(6) The apparatus for producing a bagworm silk thread according to (5), wherein the movable rail is circular.

(7) The apparatus for producing a bagworm silk thread according to any one of (1) to (6), wherein the movable rail is an automatic rail.

(8) The apparatus for producing a bagworm silk thread according to any one of (3) to (7), wherein
the collection device comprises a bobbin on the periphery thereof, and
the bobbin is configured to reel the collected bagworm silk thread.
(9) The apparatus for producing a bagworm silk thread according to (8), wherein
the bobbin comprises one or more concavities and convexities along the wind-up direction, and
the concavity and convexity are configured to receive the collected bagworm silk thread.
(10) The apparatus for producing a bagworm silk thread according to any one of (5) to (9), wherein the apparatus is configured such that the rotation of the movable rail and the collection device synchronizes with each other.
(11) A method of producing a bagworm silk thread from a bagworm, comprising a spinning process of making the bagworm hold a rail with its legs and continuously spin along the rail, wherein
the rail has a width smaller than the maximum width between the right and left legs of the bagworm for use, and is configured to be able to hold the rail with the legs of the bagworm; and
in the spinning process, the bagworm for use or a bagworm nest thereof is fixed at a position such that the legs of the bagworm can hold the rail, wherein the rail is configured to be moved in the longitudinal direction automatically and/or by the movement of the bagworm.
(12) A method of producing a long bagworm silk thread, comprising:
a spinning process of making a bagworm hold a rail with its legs and continuously spin along the rail, wherein the rail has a width smaller than the maximum width between the right and left legs of the bagworm used for thread-production, and is configured such that the legs of the bagworm can hold the rail;
a contacting process of bringing the bagworm silk thread on the rail in contact with a peeling solution and/or vapor; and
a collection process of peeling the bagworm silk thread from the rail after the contacting process to collect the bagworm silk thread,
wherein in the spinning process, the bagworm for use or a bagworm nest thereof is fixed at a position such that the legs of the bagworm can hold the rail, wherein the rail is configured to be moved in the longitudinal direction automatically and/or by the movement of the bagworm.
(13) The method according to (12), further comprising a degumming process of degumming the bagworm silk thread during the contacting process, during the collection process, and/or after the collection process.
(14) The method according to (12) or (13), further comprising a twisting process of twisting the bagworm silk thread after the collection process and/or after the degumming process.
(15) The method according to any one of (11) to (14), wherein the rail is loop-shaped.

The present specification encompasses the contents disclosed in the specification and/or drawings of Japanese Patent Application No. 2018-227669, on which the priority of the present application is based.

Effects of Invention

A method of producing a bagworm silk thread according to the present invention enables a bagworm to spin only in a given direction without giving the bagworm a burden of supporting a nest.

A method of producing a long bagworm silk thread according to the present invention makes it possible to easily and efficiently produce a pure long bagworm silk thread derived from a bagworm almost without causing a physical damage to the spun bagworm silk thread.

An apparatus for producing a bagworm silk thread according to the present invention makes it possible to automate the processes from the spinning of a long bagworm silk thread through to the collection of the thread.

BRIEF DESCRIPTION OF DRAWINGS

FIG. 2A shows how a bagworm moves while spinning a foothold silk thread (arrowhead) and hooks its claws on the foothold silk thread spun by the bagworm (thin arrow), and how the nest is open at one end of the nest for exposing a part of its body during migration (thick arrow)

FIG. 2(a) shows the front view, and FIG. 2(b) depicts the top view.

FIGS. 4(a), 4(b), and 4(c) show the periphery of a disc (0401), the rim of a wheel (0402), and a rail constituted by a tubular inner wall face (0403) respectively.

FIGS. 5(a), 5(b), and 5(c) show a structure constituted by a plurality of claw-shaped members for holding an object to be fixed, a tubular structure embedded an object to be fixed, and a structure for binding an object to be fixed to (or attached to, or seamed with) a support respectively.

FIGS. 6(a) and 6(b) show a disc-shaped bobbin and a cylindrical bobbin respectively. Both of them each show salient portions (0601) placed at the ends of the bobbin.

FIG. 7(a) shows the state where the rotation face (0702) of the loop-shaped path (0701) and the rotation face (0704) of the collection device (0703) are in parallel with each other. FIG. 7(a) also shows an example of a structure in which the collection device and the loop-shaped rail are coaxial. FIG. 7(b) shows the state where the rotation face (0702) of the loop-shaped path (0701) and the rotation face (0704) of the collection device (0703) are vertical to each other. FIG. 7(c) shows the state where the rotation face (0702) of the loop-shaped path (0701) and the rotation face (0704) of the collection device (0703) are placed side by side on the same plane.

FIGS. 8(a), 8(b), 8(c), and 8(d) show a pulley, a reeling drum, a hook, and a ring hook, respectively.

DESCRIPTION OF EMBODIMENTS

1. Apparatus for Producing Bagworm Silk Thread

1-1. Overview

A first aspect of the present invention is an apparatus for producing a bagworm silk thread. A thread-producing apparatus according to the present invention comprises a movable rail and a fixator as essential constituents, and additionally, comprises a peeling container, a collection device, and a thread hook as optional constituents. A thread-producing apparatus according to the present invention enables a bagworm to spin always in a given direction without giving the bagworm a burden of supporting a nest and through restricting the degree of freedom of the bagworm within a necessary range. Additionally, some embodiments make it possible to automate the processes from the spinning of a long bagworm silk thread through to the collection of the thread. Furthermore, the spinning process and the collection process can be performed concurrently, and thereby making it possible to achieve efficient production of a long bagworm silk thread and the accompanying decrease in production cost.

1-2. Definition

The following terms frequently used herein are defined as described below.

Figure 1:
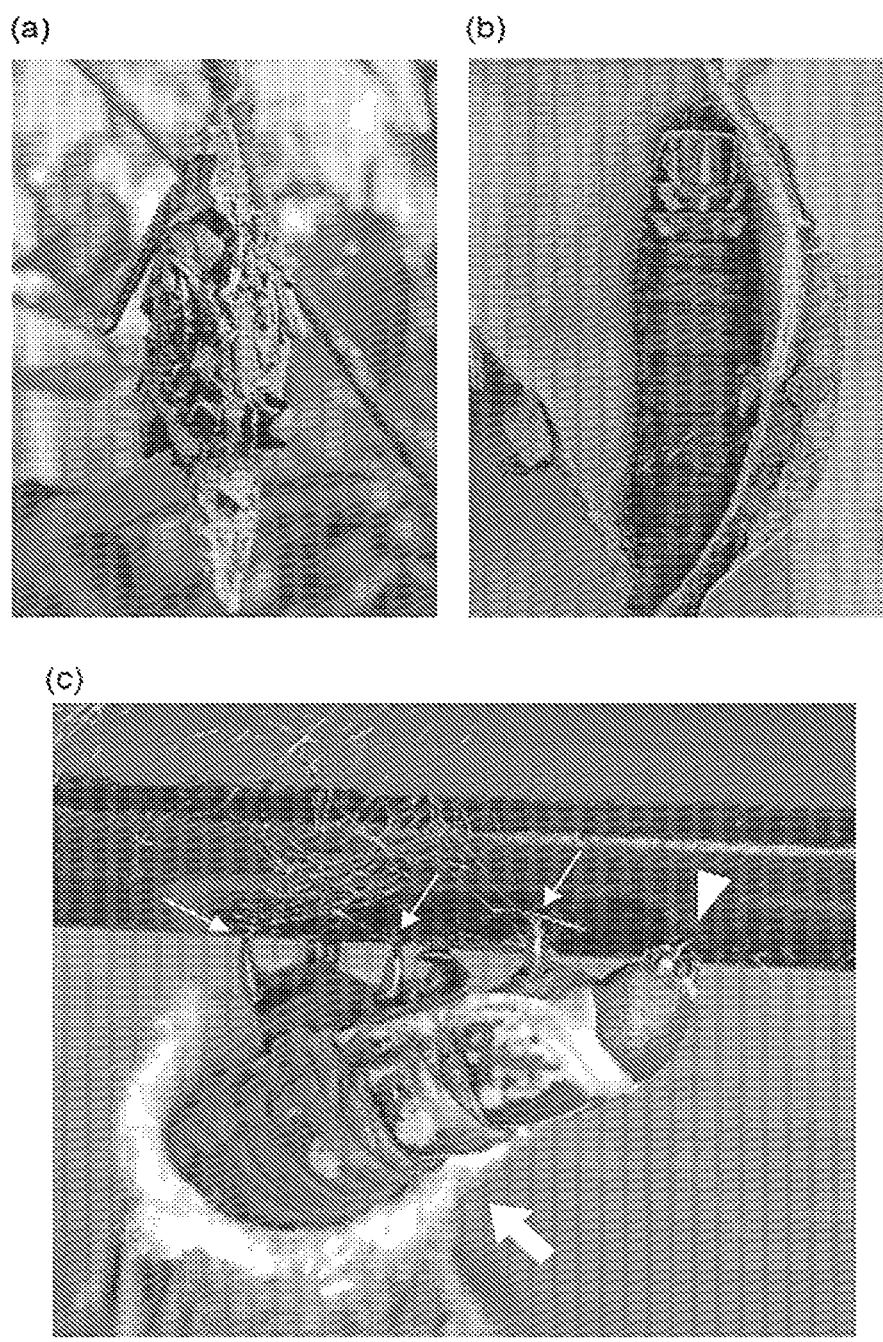
FIG. 1(a) shows the appearance of a nest of a bagworm of *Eumeta japonica* (*Eumeta japonica* bagworm).
FIG. 1(b) shows the inside of the nest of a *Eumeta japonica* bagworm, which has been cut and opened along the longitudinal axis. The worm located in the middle is an *Eumeta japonica* larva, i.e., a *Eumeta japonica* bagworm.
FIG. 1(c) shows the spinning behavior of an *Eumeta japonica* bagworm during migration.

The term "bagworm" collectively refers to a moth larva belonging to the family Psychidae in the order Lepidoptera, as described above. Moths belonging to the family Psychidae are distributed worldwide and the larva (bagworm) of any species of the moth spends the whole larval stages living in a nest covered with natural materials, such as pieces of leaves and twigs, which are assembled by silk threads spun by the larva itself. As shown in FIG. 1(a), the nest is a spindle-shaped, cylinder-shaped, or cone-shaped bag-like nest that can accommodate the whole body of a bagworm. As shown in FIG. 1(b), a bagworm usually hides itself inside the nest and always carries the nest even during eating or moving and in principle, even pupates inside the nest. When the term "nest" is simply recited herein, it means a bagworm nest, unless specifically noted.

The species, instar, and gender of bagworms used herein are not limited, as long as the bagworm is a larva of a moth species belonging to the family Psychidae and the species makes a nest as described above. For example, the family Psychidae comprises the genera *Acanthopsyche, Anatolopsyche, Bacotia, Bambalina, Canephora, Chalioides, Dahlica, Diplodoma, Eumeta, Eumasia, Kozhantshikovia, Mahasena, Nipponopsyche, Paranarychia, Proutia, Psyche, Pteroma, Siederia, Striglocyrbasia, Taleporia, Theriodopteryx, Trigonodoma*, etc., and the bagworm used herein may be a species belonging to any genus. Specific examples of bagworm moth species comprise *Eumeta japonica, Eumeta minuscula*, and *Nipponopsyche fuscescens*. The instar of the larva may be any instar between the first instar and the last instar. However, a larger bagworm is preferable to obtain a thicker and longer bagworm silk thread. For example, among larvae of the same species, a larva in the last instar is more preferable, and a female larva is more preferable than a male larva because a female grows larger than a male. Furthermore, among the family Psychidae, a larger species is more preferable. Thus, *Eumeta japonica* and *Eumeta minuscula* are species that are preferable as the species of bagworms used in the present invention.

The term "silk thread" as used herein refers to a proteinous thread from an insect, which is spun by the insect in the larval or adult stage for the purpose of nest building, migration, anchoring, cocooning, prey capture, and the like. When the term "silk thread" is simply recited herein, it means a bagworm silk thread, unless specifically noted.

The term "bagworm silk thread" as used herein refers to a bagworm-derived silk thread. The "bagworm silk thread" as used herein encompasses a monofiber, spun fiber, and fiber assembly.

The term "monofiber" as used herein, which is also referred to as monofilament, is the smallest filament unit constituting a fiber component. The monofiber contains, as a main component, a fibroin-like protein constituting a silk thread. A bagworm silk thread in a natural state is spun as a bifilament in which two monofibers are joined together by a gummy material composed of a protein. This spun bifilament is referred to as a "spun fiber". The spun fiber is degummed, thus enabling the gummy material to be removed and affording a monofiber.

The term "fiber assembly" as used herein, which is also referred to as multifilament, refers to a fiber composed of a plurality of bundles of fibers. The fiber assembly refers to a so-called raw silk thread, and is composed of a plurality of monofibers in principle. Herein, however, the fiber assembly also includes a fiber assembly composed of a plurality of monofibers and spun fibers or a plurality of spun fibers. Though the term "fiber assembly" as used herein can encompass a fiber mixture composed of a mixture of a bagworm silk thread and another fiber such as a silkworm silk thread, the term is intended herein to mean a fiber assembly composed of a bagworm silk thread alone, unless specifically noted. The fiber assembly is twisted by a twisting process to become a stronger silk thread. However, the fiber assembly in this specification encompasses not only a twisted fiber assembly but also a non-twisted fiber assembly exhibiting a flexible and smooth texture.

The bagworm silk thread comprises a foothold silk thread and a nest silk thread. The "foothold silk thread" refers to a silk thread spun by a bagworm spins in advance of migration and a function as a foothold for preventing fall from a branch, leaf, or the like during migration. As shown in FIG. 1(c), a bagworm usually uses a foothold silk thread as a foothold and hooks its claws onto the foothold silk thread to move in the direction of migration. A foothold silk thread is spun by a bagworm swinging its head right and left, and every time the head is swung, the silk thread is fixed to twigs and leaves as a base with the above-mentioned gummy material, and thus, is usually spun in a zigzag pattern. This structure makes it easier for the bagworm to hook the right and left legs onto the foothold silk thread, and causes the load on the silk thread fixation portion or the silk thread itself to be distributed right and left. On the other hand, the "nest silk thread" refers to a silk thread forming a nest, which is spun to assemble pieces of leaves and twigs or to make an inner wall of a nest so that its accommodation space can become a comfortable environment. In principle, a foothold silk thread is thicker and also mechanically stronger than a nest silk thread.

As used herein, the term "long" refers to a length longer than the normal length in the art. As used herein, the term "long" especially refers to being longer than the length of a spun silk threads (a length of less than 1 m) obtainable from a bagworm using conventional technology. Specifically, the term "long" refers to 1 m or more, preferably 2 m or more, more preferably 3 m or more, 4 m or more, 5 m or more, 6 m or more, 7 m or more, 8 m or more, 9 m or more, or 10 m or more. The upper limit of the length is not particularly limited, but corresponds to the length of a silk thread which a bagworm can continuously spin. For example, the length is 1.5 km or less, 1 km or less, 900 m or less, 800 m or less, 700 m or less, 600 m or less, 500 m or less, 400 m or less, 300 m or less, 200 m or less, or 100 m or less. The length of a spun fiber of a bagworm silk thread is also the length of a monofiber constituting the fiber, and corresponds to the length of the thread continuously spun by a bagworm. Therefore, a longer bagworm silk thread can be obtained if it is possible to make a bagworm spin a thread continuously.

As used herein, the term "thread-producing (or producing a thread)" refers to make a bagworm spin a silk thread for the purpose of obtaining a bagworm silk thread. For a thread-producing apparatus according to the present invention, however, "thread-producing" can comprise not only spinning but also collecting the spun silk thread. In the present specification, a bagworm silk thread to be produced is a foothold silk thread.

The term "leg" as used herein refers to an entire leg or a part of a leg of a bagworm. Legs called thoracic legs extend from the thorax of a bagworm, as shown by the arrows in FIG. 1(c). The thoracic legs consist of three legs (front, middle, and rear legs) located on each side, which means three pairs of right and left legs, with a total of six legs.

The term "hold" generally refers to hooking and holding, but herein refers to that a bagworm holds its legs on a rail to move on the rail. A bagworm usually uses its legs to catch a twig or a leaf to support the whole or a part of the weights of itself and a nest. That is, although the meaning of "hold" comprises preventing a bagworm itself and its nest from falling, in the present invention, a bagworm is fixed and does not need supporting its own weight. Accordingly, the meaning of "hold" as used herein does not encompass supporting a bagworm's own weight, in principle. In this regard, a bagworm is free to catch or release an object, and does not mean that the legs which have once caught an object become fixed at the holding position. A bagworm uses its legs to repeat catching and releasing a rail so that the bagworm can freely move on a rail.

1-3. Constitution

Figure 2:
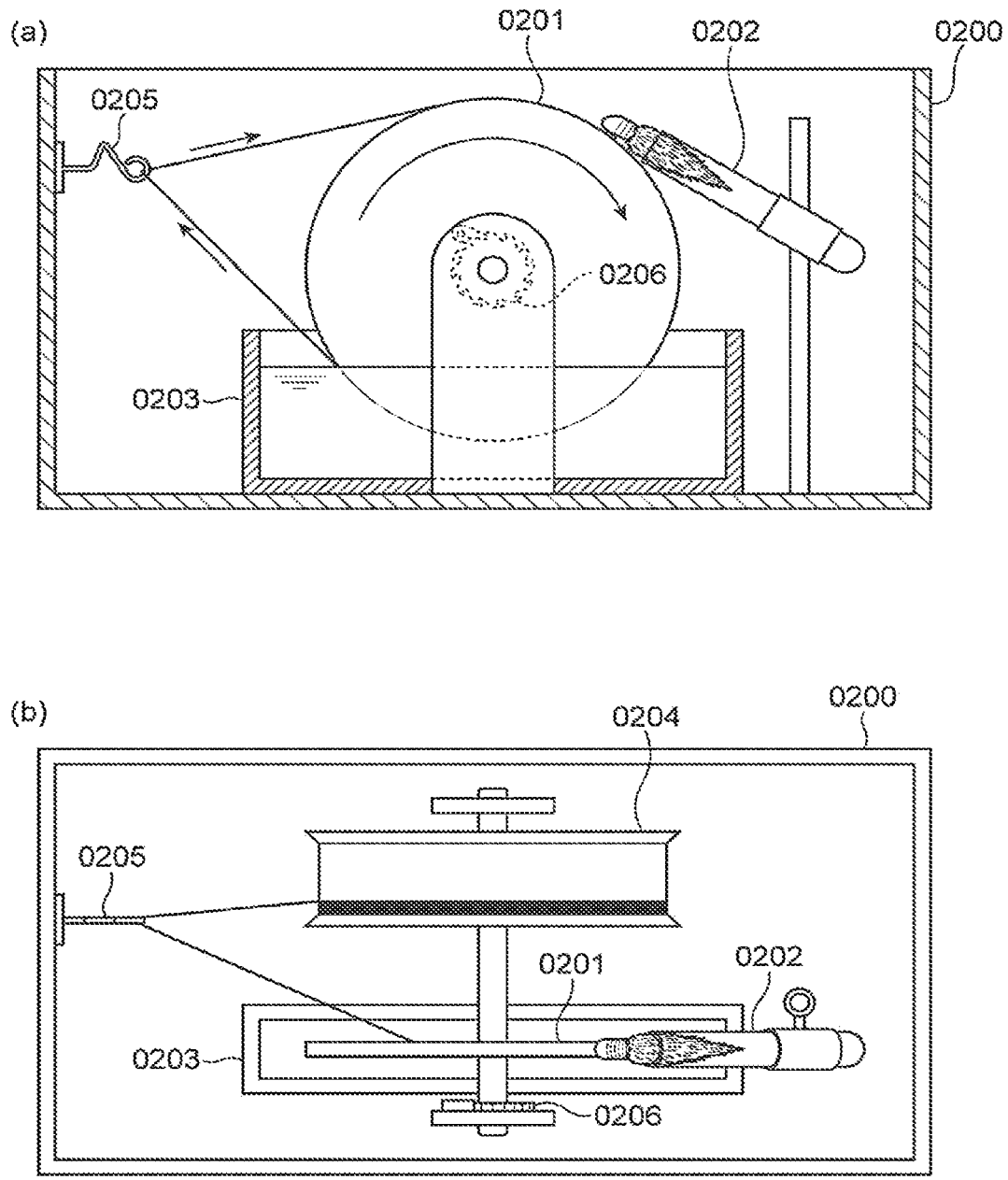
FIG. 2 shows a schematic of an apparatus for producing a bagworm silk thread according to the present invention.

FIG. 2 is a schematic diagram of a thread-producing apparatus according to the present invention. As shown in this diagram, a thread-producing apparatus (0200) according to the present invention comprises a movable rail (0201) and a fixator (0202) as essential constituents, and comprises a peeling container (0203), a collection device (0204), and a thread hook (0205) as optional constituents. Each of the constituents will be described below.

1-3-1. Movable Rail

A "movable rail" (0201) is a rail configured to move in the longitudinal direction, and is an essential constituent in a thread-producing apparatus according to the present invention. The movable rail may comprise a ratchet (0206), if necessary.

(1) Constitution of Rail

A "rail" as used herein refers to a path with a linear structure on which a bagworm moves. The "linear structure" as used herein refers to a single-rail structure with a same or substantially same width, whose cross-sectional shape is not limited to any particular shape, but comprises circular shapes, approximately circular shapes (comprising oval shapes), polygonal shapes (comprising square and approximately square shapes), and combinations thereof.

The width of a rail is made less than the maximum width between the extended legs of a bagworm used for a thread-producing apparatus according to the present invention. The "width of a rail" as used herein refers to the length of a moiety of the rail, which is directly related to holding legs of a bagworm on the rail when the legs of the bagworm hold the rail. This length generally corresponds to the transverse (short axis) length of the rail. The maximum width of the rail is less than the maximum width between the extended legs of a bagworm used for the thread-producing apparatus according to the present invention. On the other hand, the minimum width of the rail is not limited to any particular length, as long as a bagworm can hold the legs on the rail. For example, the rail may be on the edge of a thin metal plate with a thickness of around 0.5 mm. In the rail shown in FIG. 3A, the cross-sectional diameter ($\varphi$) corresponds to the width of the rail.

Figure 3:
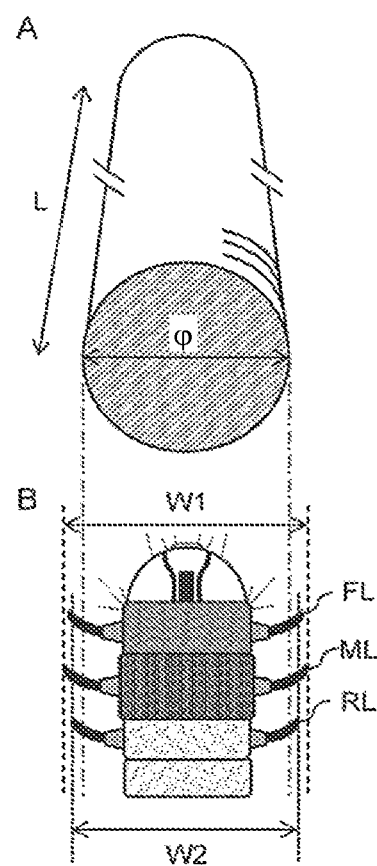
FIG. 3A shows a schematic of a rail in an apparatus for producing a bagworm silk thread according to the present invention. This figure shows a rail having a circular cross section. In the figure, L and φ represent the length of the rail in the longitudinal axis and the cross-sectional diameter of the rail respectively. In the rail, φ corresponds to the width of the rail.
FIG. 3B shows a dorsal view of the head and thorax of a bagworm spreading out the legs to the left and right at the maximum width. In the figure, FL, ML, and RL represent the front legs, middle legs, and rear legs, respectively. W1 and W2 represent the maximum width between the left and right legs when the bagworm spreads out its legs, for middle legs and posterior legs, respectively.

The "maximum width between the extended legs of a bagworm" as used herein refers to the width (W1 or W2) between the right and left legs of the bagworm, which are extended right and left as much as possible, as shown in FIG. 3B. A bagworm has three pairs of right and left legs (front, middle, and rear legs), and the maximum width between the extended legs preferably represents either of the maximum widths except for the longest (maximum) width between the extended legs, namely the second longest width or the shortest width between the extended legs. The maximum width more preferably represents the shortest (minimum) width between the extended legs. In FIG. 3B, the maximum width (W1) between the extended middle legs (ML) is the longest, and the maximum width (W2) between the extended rear legs (RL) is the shortest among the three pairs of legs. Therefore, when the width of a rail is determined, the maximum width between the extended front legs or between the extended rear legs, particularly the maximum width between the extended rear legs, W2 is preferable as the maximum width between the extended legs of a bagworm. The maximum width between the extended legs varies depending on the species, male and female, and instar of larvae, but generally falls within a specific range if the bagworms are the same species of nearly the same instar. For example, in *Eumeta japonica*, the maximum width between the extended legs of young instar bagworms (around the first to third instar) ranges from 2 mm to 4 mm or from 3 mm to 5 mm. That of the middle instar larva (around the fourth to fifth instar), ranges from 3 mm to 7 mm or from 4 mm to 8 mm. That of the penultimate instar larva or last instar larva ranges from 4 mm to 9 mm, from 5 mm to 10 mm, or from 6 mm to 12 mm i. In *Eumeta minuscula*, the maximum width between the extended legs of young instar larva (around the first to third instar) ranges from 1.5 mm to 3.5 mm. That of the middle instar larva (around the fourth to fifth instar) ranges from 2.5 mm to 6 mm or from 3 mm to 7 mm. That of the penultimate instar larva or last instar larva ranges from 3.5 mm to 8 mm, from 4 mm to 9 mm, or from 5 mm to 10 mm. Thus, the width of the rail should be changed as appropriate according to the species, instar, and male and female of a bagworm for use. In each larval instar, the width of the rail is preferably less than the shortest (minimum) among the maximum widths between the extended legs of a bagworm of the species used, in terms of holding legs as described below.

The rail is configured such that the legs of a bagworm can hold a rail. The expression "the legs can hold" refers to having a structure such that the legs of a bagworm can hold a rail. Any of the legs may hold a rail. Examples of such a manner comprise: a manner in which at least a pair of legs, one each from the right and left sides, among the six legs, that is, the three pairs of legs, of a bagworm hold a rail between the legs; and a manner in which two or three legs on either the right or left side of a bagworm hold a rail in such a manner that the rail runs beneath the thorax. If the legs of a bagworm can hold a rail, the bagworm can move along the rail, spinning a foothold silk thread on the rail.

The rail is not limited to any particular entire shape or length. The rail may have an end, or may be a loop-shaped rail having no end. For a long silk thread to be produced using a rail having an end, the longer the rail, the more preferable. On the other hand, a rail which is a loop-shaped rail having no end makes it possible that a bagworm circles around the rail to obtain a long silk thread, and thus, such a rail may have a limited length. To make a bagworm continue to spin, the rail is preferably a loop-shaped rail having no end. The loop portion of a loop-shaped rail may be a closed loop or an open loop. However, in cases of the open loop, a gap in the open loop portion should have a width such that a bagworm for use can go across the gap. Such a gap may exist at a plurality of positions in an open loop-shaped rail. Additionally, examples of the entire shape of a loop-shaped rail comprise circular shapes, approximately circular shapes, square shapes, approximately square shapes, polygonal shapes, indefinite shapes, and combinations thereof. A circular loop-shaped rail with a circular shape, or an elliptical loop-shaped rail with an approximately circular shape is preferable.

Figure 4:
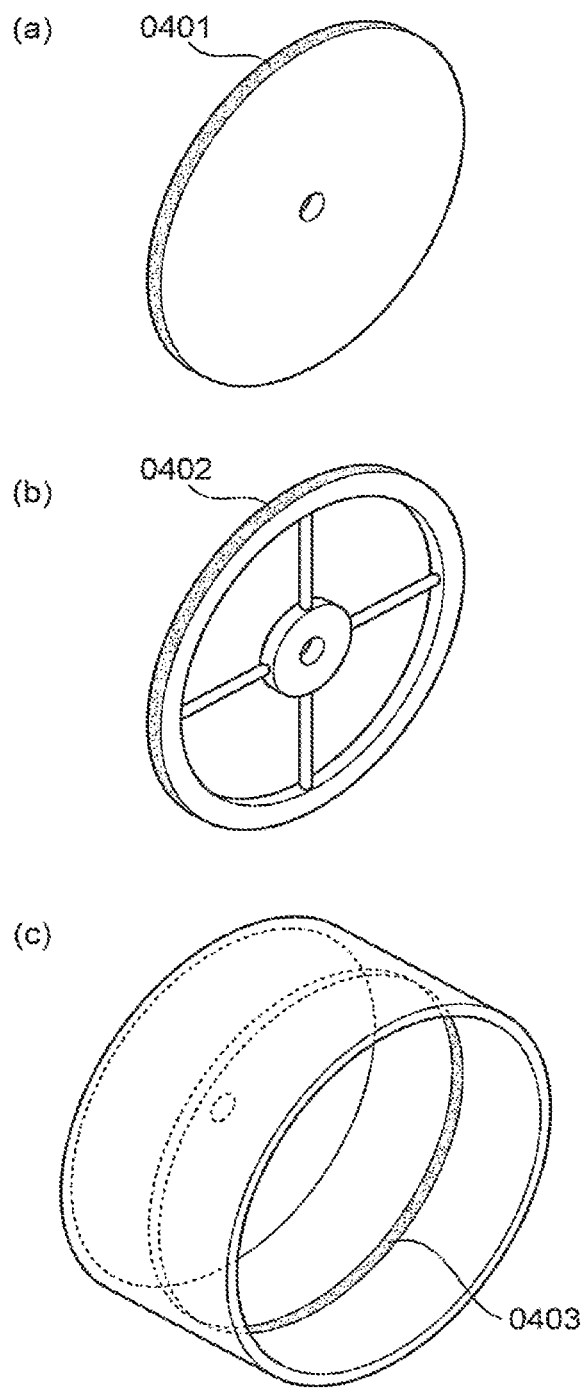
FIG. 4 shows a specific example of a loop-shaped rail in an apparatus for producing a bagworm silk thread according to the present invention.

Specific examples of circular loop-shaped rails comprise the periphery of a disc (0401) shown in FIG. 4(*a*), the rim of a wheel (0402) shown in FIG. 4(*b*), and a rail (0403) constituted by a tubular inner wall face shown in FIG. 4(*c*).

A rail constituted by the periphery of a disc (0401) refers to a rail constituted by the periphery of a circular plate-like member. In this case, the thickness of the disc corresponds to the width of the rail. The diameter $\varphi$ of the disc may be in, but is not limited to, the range of from 5 cm to 50 cm, from 10 cm to 30 cm, from 15 cm to 25 cm, or from 17 cm to 20 cm.

A rail constituted by the rim of a wheel (0402) refers to a rail constituted by circularizing a rod-like member, such as a wire. In this case, the diameter or transverse width of the rod-like member corresponds to the width of the rail. As with the diameter of the above-mentioned disc, the diameter $\varphi$ of the wheel may be in, but is not limited to, the range of from 5 cm to 50 cm, from 10 cm to 30 cm, from 15 cm to 25 cm, or from 17 cm to 20 cm.

A rail constituted by a tubular inner wall face (0403) refers to a rail configured by a part of a tubular inner wall face. This part is constituted as a loop-shaped salient along the tubular internal circumferential face, and has a structure in which the transverse width of the salient corresponds to the width of the rail. The diameter $\varphi$ of the tubular internal circumference may be in, but is not limited to, the range of from 10 cm to 60 cm, from 15 cm to 50 cm, from 20 cm to 40 cm, or from 25 cm to 30 cm.

The material of the rail is not limited. For example, metals, ceramics (comprising enamel), glass, stones, resins (comprising synthetic and natural resins), wood materials (comprising branch, vine, bamboo, and the like), fibers, bones and fang, and combinations thereof can be used. The material preferably has a sufficient strength to be invulnerable to the biting attack of a bagworm. For example, metals, ceramics, glass, stones, and the like are preferable. Additionally, a portion of a rail to which a bagworm silk thread is adhered is preferably made from a material with a smooth surface to facilitate collection of a bagworm spun silk thread. The "material with a smooth surface" as used herein refers to a material processable to form a smooth surface, such as metals, glass, and plastics. Additionally, any material coated with a paint or the like to obtain a smooth surface is included in the material with a smooth surface, even if the original material is difficult to polish for the formation of a smooth surface, such as wood materials and fibers. When the rail is the periphery of a plate-like member, the plate-like member and the periphery may be made from the same material or from different materials.

The thread-producing apparatus can comprise a plurality of rails. The conditions such as the shapes and materials of the rails may be the same or be different, or may be a combination thereof. Examples comprise rails configured by the peripheries of a plurality of coaxial discs placed in parallel. With a thread-producing apparatus with such rails, by fixing a plurality of bagworms, on each rail, it possible to make the bagworms spin a plurality of bagworm silk threads concurrently, immediately followed by twisting and collecting the threads.

A rail in a thread-producing apparatus according to the present invention may have a slope relative to a horizontal plane. The slope angle is not limited to any value. For example, when the rail is configured by the periphery of a disc, and if the planar portion of the disc member as a base is placed horizontally, the slope angle of the rail is 0 degrees. On the other hand, when the planar portion of the disc member is placed vertically, the rail can encompass every slope angle.

(2) Constitution of Movable Rail

A "movable rail" is configured such that the rail moves in the longitudinal direction. The "longitudinal direction" as used herein refers to the direction along the long axis of the rail. For example, in cases of a circular loop-shaped rail constituted by the periphery of a disc, the whole disc member has a rotatable structure.

Without limitation, the movable rail is configured to move so as to synchronize with the movement of a bagworm spinning in the direction of movement on the rail. Accordingly, a force required for the initial motion of the rail should be equal to or less than a movement impelling force generated when a bagworm moves on the rail. Examples of powers for driving a rail comprise a movement impelling force of a bagworm, electrical power, and the like.

A "movement impelling force of a bagworm" is an impelling force generated by the legs of a bagworm moving along the rail. In a thread-producing apparatus according to the present invention, a bagworm is fixed by the below-mentioned fixator. Accordingly, even if the bagworm moves, spinning on the rail, it substantially cannot advance in the direction of movement. The movement impelling force generated by the movement of the bagworm can drive the rail as a force acting in the direction opposite to the direction of movement of the bagworm. In the present specification, this force is referred to as the movement impelling force of a bagworm.

On the other hand, the rail can be configured to be automatically driven by an electrical power via a motor, a gear, and the like. The direction of movement of this automatic rail is opposite to the direction of movement of a bagworm. Additionally, the moving speed of the rail is preferably approximately equal to or less than the moving speed of a bagworm. The specific moving speed of a bagworm varies depending on the kind, instar, individual size, and the like of the bagworm, and is usually in the range of from 3 m/hr to 15 m/hr, or in the highest range of from 17 m/hr to 22 m/hr. Accordingly, the automatic rail may be moved at a moving speed (v) equal to or less than these speeds. For example, the moving speed may be as follows: $0$ m/hr$<v\leq 22$ m/hr, $0$ m/hr$<v\leq 20$ m/hr, $0$ m/hr$<v\leq 17$ m/hr, $0$ m/hr$<v\leq 15$ m/hr, $0$ m/hr$<v\leq 12$ m/hr, $0$ m/hr$<v\leq 10$ m/hr, $0$ m/hr$<v\leq 8$ m/hr, $0$ m/hr$<v\leq 5$ m/hr, $0$ m/hr$<v\leq 4$ m/hr, or $0$ m/hr$<v\leq 3$ m/hr. In cases of using an automatic rail, the movement impelling force of a bagworm concurrently acts on the rail during spinning. That is, the automatic rail is a mechanism for assisting a bagworm in moving. In this case, since a driving force of the automatic rail is added, a burden on a bagworm moving can be significantly alleviated.

(3) Ratchet

The movable rail may comprise a "ratchet" (0206) as an optional constituent. The "ratchet" is a portion for restricting the direction of action to one direction. Without limitation, the ratchet is usually constituted by: a gear with teeth slanted in a given direction; and a pallet placed so as to lock the teeth. The structure is such that, when the gear rotates reversely, the pallet locks the teeth of the gear, thereby the gear can be rotated only in the given direction.

In a thread-producing apparatus according to the present invention, by synchronizing the action of the movable rail with that of the gear each other, the movable rail can move only in one direction. For example, when the movable rail is constituted by the periphery of a disc, making the disc and the gear be coaxial enables the disc to be rotated only in the direction of rotation allowed by the ratchet. Comprising this portion makes it possible that the movable rail is not moved even though a bagworm holding the rail moves backward, thereby the spinning direction is not changed and always kept in a given direction.

1-3-2. Constitution of Fixator

A "fixator" (0202) is a holder for fixing a bagworm to be used for thread-producing, and is an essential constituent in a thread-producing apparatus according to the present invention. The fixator is configured to fix a bagworm at a predetermined position in a thread-producing apparatus according to the present invention. The fixator restricts the free movement of a bagworm based on the bagworm's own intention in the apparatus, except that the bagworm moves on the rail and goes into and comes out of a nest. Accordingly, a change in the direction of movement of a bagworm and the runaway of the bagworm from the rail during spinning are restricted.

Figure 5:
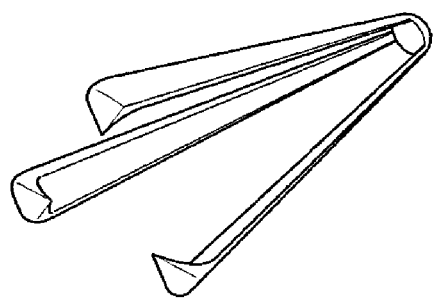
FIG. 5 shows a schematic of a fixator in an apparatus for producing a bagworm silk thread according to the present invention.
Figure 5:
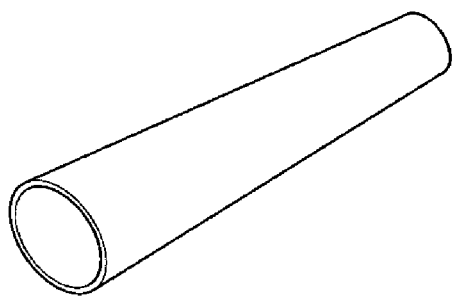
Figure 5:
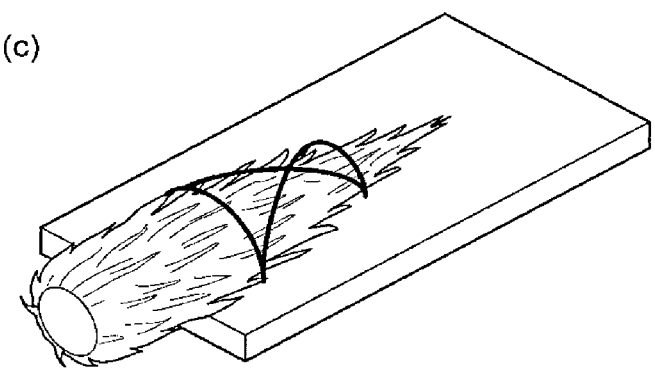

The method for fixing of a bagworm is not limited. Examples of the fixing method comprise: a structure constituted by a plurality of claw-shaped members for holding an object to be fixed as shown in FIG. 5(*a*); a tubular structure into which an object to be fixed is to be fitted as shown in FIG. 5(*b*); and a structure in which an object to be fixed is to be bonded to (or attached to or seamed with) a support as shown in FIG. 5(*c*). However, any structure can be used, as long as the structure can fix an object. A fixation adjustment portion for finely adjusting a fixing force may be comprised so that a bagworm as an object to be fixed is subjected to no excessive burden or pressure when the bagworm is fixed.

The object to be fixed is either the bagworm nest (on the premise that the bagworm exists inside the nest) or a bagworm itself. The object is preferably the nest. This is because a bagworm separated from the nest falls under excessive stress by continuing a naked state, posing the possibility of having an influence on the amount of spinning and the efficiency of spinning.

In a thread-producing apparatus according to the present invention, the fixator is placed at a position at which the fixed bagworm can hold the above-mentioned movable rail. The fixator may comprise a position adjustment portion which makes the position of a fixed bagworm adjust right and left and backward and forward to place the fixed bagworm at the position at which the legs of the bagworm can just hold the rail.

1-3-3. Constitution of Peeling Container

A "peeling container" (0203) is a container which can store a peeling solution and/or vapor. The peeling container is an optional constituent in a thread-producing apparatus according to the present invention, but is preferably equipped to produce a long bagworm silk thread.

In a thread-producing apparatus according to the present invention, the peeling container is placed in such a manner that a part of the movable rail can come in contact with the peeling solution and/or vapor in the peeling container.

The peeling container is not limited to any shape or size. Examples of peeling containers comprise: a reservoir (0203) having a size which enables a part of the movable rail to be immersed in a solution stored in the reservoir; a large peeling container such as storage room, having a size which enables a part of the movable rail to be exposed to vapor in the container; and small and medium-sized peeling containers such as a member in which a solution or vapor stored in the container can be dripped or spouted onto a part of the movable rail.

A material of the peeling container is not limited, as long as the peeling container, especially the inner wall of the peeling container, is neither dissolved, corroded, nor modified by the peeling solution or vapor. The material can be suitably selected in accordance with the kind of the peeling solution or vapor to be stored. For example, when high-temperature and high-pressure vapor is stored, a metal such as copper or stainless steel is preferable. Furthermore, when the peeling container stores a peeling solution composed of an aqueous solution containing a surfactant plastic, ceramics (enamel), glass, or the like is preferable.

The peeling container can comprise a supply port for suppling a peeling solution or vapor into the peeling container, and/or a discharge port for discharging a peeling solution or vapor out of the peeling container. The peeling container can also comprise an inflow port for suppling a peeling solution into the peeling container and/or a discharge port for discharging a peeling solution out of the peeling container.

A thread-producing apparatus according to the present invention may comprise one or a plurality of peeling containers. In cases of a plurality of peeling containers, the shapes and sizes of the peeling containers may be the same or different, or may be a combination thereof. For example, it is possible to comprise one peeling container in the form of a reservoir and three peeling containers in the form of a storage tank. Additionally, in the case of equipping a plurality of peeling containers, the conditions such as the kind, volume, and temperature of the peeling solution or vapor stored in each peeling container can be independently selected for each peeling container. For example, it is possible to equip a peeling container in the form of a reservoir storing water vapor and a peeling container in the form of a storage tank storing an soaking solution.

The peeling solution and vapor stored in the peeling container has the effect of peeling a bagworm silk thread from the movable rail or the effect of enhancing the peeling. When a bagworm silk thread is spun, the fiber component (fibroin protein) of the silk thread is fixed on the movable rail with a gummy material (sericin-like protein) secreted together. Accordingly, the above-mentioned effect is an effect which vanishes or diminishes the adhesive effect of this gummy material. The peeling solution and vapor desirably have not only the above-mentioned effect but also the property of causing no chemical and/or physical damage or being less likely to cause such damage to a bagworm silk thread. In this regard, the gummy material is composed of water-soluble protein.

The peeling solution and vapor are not limited to as long as the peeling solution and vapor have the above-mentioned effect and property. For example, the peeling solution may be, but is not limited to, water or an aqueous solution. Examples of aqueous solutions comprise surfactant solutions, buffers, and sodium bicarbonate solutions. The peeling solution is preferably water or a surfactant solution having a temperature of 20° C. or more, 25° C. or more, 30° C. or more, or 45° C. or more.

A "surfactant solution" refers to a solution of a surfactant dissolved in a preferable solvent. Examples of solvents comprise water (comprising distilled water, sterile water, and deionized water), physiological saline, and phosphate buffers. Water is preferable. The concentration of a surfactant in a solution may be, but is not limited to, 0.01% to 10%, 0.05% to 5%, 0.1% to 2%, or 0.5% to 1% in terms of % by volume.

A surfactant to be used for the surfactant solution is not limited. For example, the surfactant may be any of the following: nonionic surfactants such as Triton X-100, Triton X-114, NP-40, Brij-35, Brij-58, Tween-20, Tween-80, octyl-β-glucoside, and OTG; high molecular weight nonionic surfactants such as a copolymer of PEG and PPG; anionic surfactants such as SDS; zwitterionic surfactants such as CHAPS and CHAPSO; and combinations thereof.

Additionally, the vapor may be water vapor.

1-3-4. Constitution of Collection Device

A "collection device" (0204) is configured to collect a bagworm silk thread peeled from the movable rail. The collector is an optional constituent in a thread-producing apparatus according to the present invention, but is preferably equipped to produce a long bagworm silk thread.

The collection device is not limited to any structure as long as the collection device has a structure which enables the peeled bagworm silk thread to be gathered and retained. The collection device preferably has a structure equipping a bobbin.

The "bobbin" is a portion equipped in the collection device, and is configured to reel a thread collected around the periphery thereof. Additionally, the bobbin can itself be rotatably configured to reel a thread. The driving force for rotation can be, for example, an electrical power obtained via a motor or the like. Alternatively, the driving force can be obtained via a movement impelling force generated by a bagworm moving on the rail. The movement impelling force can be obtained, for example, by making a loop-shaped rail coaxial with the collection device as in FIG. 7(a) or by conveying the movement of a movable rail to the collection device via a gear (comprising a worm gear), a belt (comprising a timing belt), or the like.

The bobbin is not limited to any particular shape as long as a thread can be reeled around the periphery of the bobbin. For example, the bobbin may be in the form of any one of a disc, cylinder, rectangular column (comprising a plurality of rod members which each constitute each longitudinal edge of a rectangular column), plate, or combination thereof.

As the material of the bobbin, for example, a metal, resin (comprising a synthetic resin and a natural resin), wood material (comprising a branch, bine, bamboo, and the like), ceramics, stone, or combination thereof can be utilized. The material preferably makes it possible that the portion which comes into contact with a reeled bagworm silk thread is processed into a curved face and/or a smooth face such that the thread is not damaged.

Figure 6:
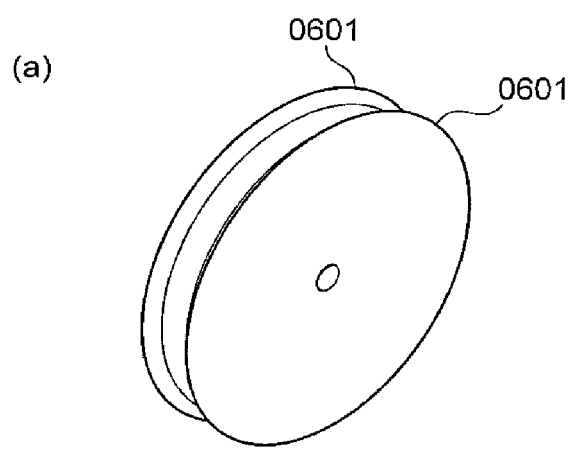
FIG. 6 shows an example of the shape of a bobbin set up on the periphery of a collection device.
Figure 6:
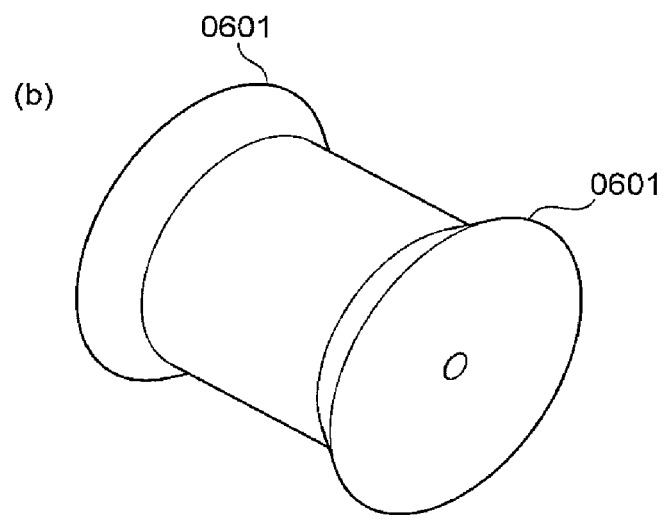

The bobbin can comprise one or more concavities and convexities. The "concavity and convexity" are configured along the longitudinal direction of the bobbin, and configured such that the collected bagworm silk thread is received in the concavity, and such that the bagworm silk thread does not fall off from the collection device. For example, when the bobbin is disc-shaped (FIG. 6 (a)) or cylindrical (FIG. 6 (b)), the bobbin equips salient portions (0601) at the ends, as shown in FIG. 6.

Figure 7:
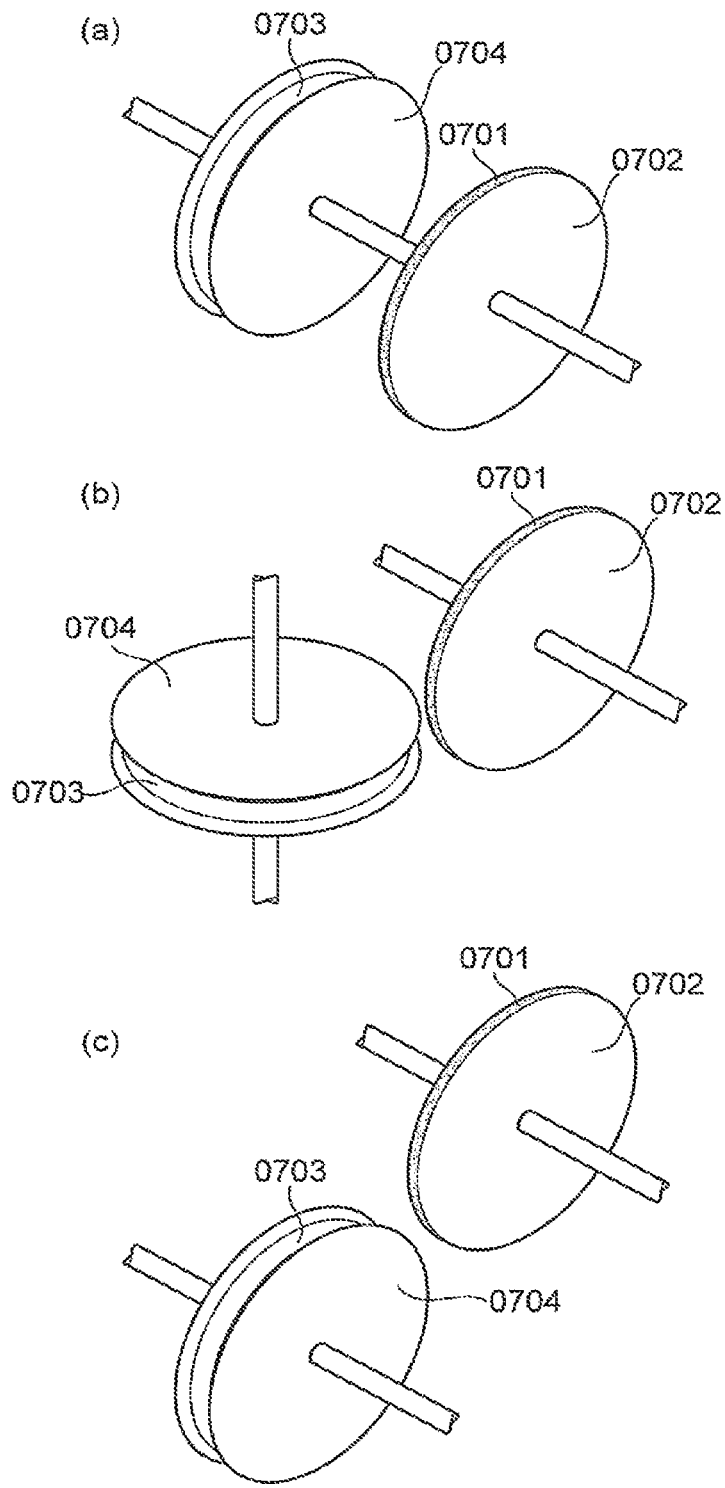
FIG. 7 shows an example of the disposition of a loop-shaped rail and a collection device.

When the collection device comprises a bobbin and where the movable loop-shaped path is a loop-shaped rail (0701) as in FIG. 7, the rotation face (0702) of the loop-shaped path and the rotation face (0704) of the collection device (0703) may be in parallel with each other, as shown in FIG. 7(a), or may make another angle between the rotation faces (for example, may be vertical to each other as shown in FIG. 7(b), or may be placed side by side on the same plane, as shown in FIG. 7(c)). The direction of rotation of the bobbin and the direction of movement of the movable rail may be the same or different, for example, the opposite directions. The collection device can be configured such that the rotation of the collection device synchronizes with that of the loop-shaped rail. For example, as shown FIG. 7(a), making the collection device be coaxial with the loop-shaped rail, an identical and synchronized direction of rotation can be achieved.

1-3-5. Constitution of Thread Hook

The "thread hook" (0205) is configured to change the thread reeling direction of a bagworm silk thread peeled from the movable rail. In a thread-producing apparatus according to the present invention, the thread hook is placed mainly between the movable rail and the collection device for collecting the peeled bagworm silk thread, and is used for the purposes of changing the reeling direction of the bagworm silk thread, adjusting the reeling position, and the like. Additionally, the thread hook can equip a function for giving tension to a bagworm silk thread and collecting slack generated between peeling and collecting.

Figure 8:
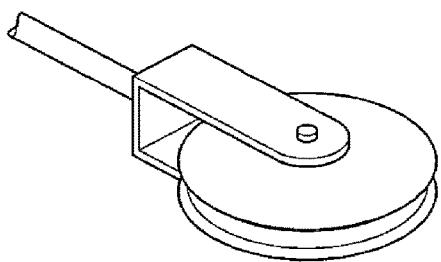
FIG. 8 shows an example of the shape of a thread hook.
Figure 8:
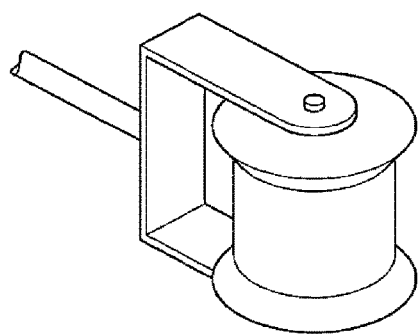
Figure 8:
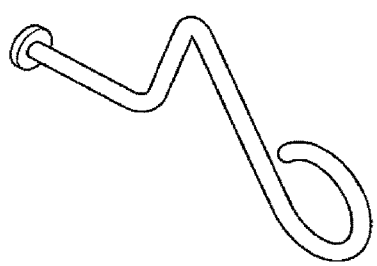
Figure 8:
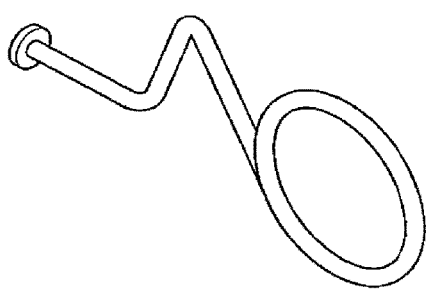

The thread hook is not limited to any shape as long as the thread hook is shaped so as not to damage a thread, and be able to change the thread reeling direction without giving a burden. Examples of the shape comprise a pulley (a), a reeling drum (b), a hook (c), a ring hook (d), and the like, as shown in FIG. 8. A tension spring or the like may be added to the thread hook with a function for giving tension to a bagworm silk thread.

As the material of the thread hook, for example, a resin (comprising a synthetic resin and a natural resin), metal, wood material (comprising a branch, bine, bamboo, and the like), ceramics, stone, or combination thereof can be utilized. A portion in contact with the bagworm silk thread is desirably processed into a curved face and a smooth face to prevent a thread from tearing by physical damage and friction.

When the thread-producing apparatus equips a plurality of thread hooks, the thread hooks may be the same or different.

In the thread-producing apparatus, the thread hook is placed and fixed at a position suitable for changing the thread reeling direction of the peeled bagworm silk thread to a desired direction.

2. Method of Producing Bagworm Silk Thread 2-1. Overview

A second aspect of the present invention is a method of producing a bagworm silk thread. A thread-producing method according to the present invention comprises a spinning process as an essential process. A thread-producing method according to the present invention makes it possible to decrease a burden on a bagworm spinning a thread, and keep the spinning direction in a given direction. As a result, it is possible to efficiently produce a long bagworm silk thread without needing a special skill.

2-2. Method

The method according to the present invention comprises a spinning process as an essential process. The spinning process will be specifically described below.

The "spinning process" is a process of making a bagworm hold its legs on a rail and continuously spin a thread in the direction along a rail under the active conditions of the bagworm.

The term "active conditions" as used herein refers to conditions under which a bagworm can perform activities involving usual movements such as migration and eating. Such conditions include, for example, temperature, atmospheric pressure, humidity, brightness, and oxygen level, and the most important condition in the present invention is temperature. Since insects are poikilotherms, they suspend activities and enter into dormancy as the air temperature decreases. Thus, among the active conditions in the present invention, the lower limit of the preferable air temperature is a temperature at bagworm do not enter into dormancy. The specific temperature varies depending on the species, and may be generally 10° C. or more, preferably 12° C. or more, more preferably 13° C. or more, still more preferably 14° C. or more, still more preferably than 15° C. or more. On the other hand, the upper limit of the temperature is the upper limit of temperature under which a bagworm can survive. In general, the temperature may be 40° C. or less, preferably 35° C. or less, more preferably 30° C. or less, still more preferably 27° C. or less, still more preferably 25° C. or less. The atmospheric pressure, humidity, brightness, oxygen concentration, and the like may be substantially equal to, for example, those in plains in temperate areas. For example, the atmospheric pressure is around 1 atmosphere, the humidity ranges from 30 to 70%, and the brightness is maintained for 6 hours to 18 hours out of 24 hours, and the concentration of oxygen in the atmosphere ranges from 15 to 25%.

A bagworm used in this process may be a bagworm collected in the field or alternatively a bagworm bred in successive generations under artificial conditions. Preferably, neither of the bagworms is fasted, and more preferably, either is fed much before use. If a bag worm used in this process is not starved but is fed sufficiently, the bagworm continuously spins a thread with moving on a rail under the above-described conditions for a period from 1 hour to 4 days, from 3 hours to 3 days, or from 6 hours to 2 days.

A bagworm used in this process may be having a nest or may be left out of a nest. Since a bagworm generally behave with a nest, the bagworm in a nest is suitably used in this process. For example, however, when a bagworm is used in the present process with a tubular fixator in which the naked bagworm taken out of a nest is received, the bagworm does not need to hold a nest. When a bagworm holds a nest, the nest does not need to be intact, as long as the nest can hide almost the whole body of the bagworm. The nest is not necessarily composed of natural materials such as pieces of leaves and twigs and may be created using artificial materials (such as paper pieces, wood chips, discrete fibers, metal pieces, plastic pieces, and the like).

The present process is characterized in that a bagworm is fixed at a position at which the legs of the bagworm can hold the rail. This fixation restricts the free movement of the bagworm, thus making it possible to fix the spinning direction on the rail to a given direction. In this regard, one bagworm is placed and fixed on one rail in principle, but a plurality of bagworms can be fixed on one rail. In this case, the bagworms are placed and fixed on a rail in such a manner that the bagworms move in the same direction.

The constitution and structure of a rail to be used for a thread-producing method according to the present invention may comply with a constitution and structure of the rail in the apparatus for producing a bagworm silk thread as described in the first aspect. The structure is preferably a loop-shaped rail, especially a circular loop-shaped rail. A plurality of rails may be used. In this case, the rails may be placed in parallel so that each bagworm can be fixed in such a manner that the legs of each bagworm hold each rail. The bagworm is fixed using a fixator or the like. The fixator may be constituted as described in the first aspect. Once a bagworm is allowed to hold a rail under the active conditions, the bagworm will continuously spin a thread while spontaneously moving along the rail.

The phrase "continuously spin a thread" as used herein refers to a bagworm's spinning a thread without interruption. A bagworm holding a rail with the legs continues to spin a foothold silk thread by instinctive nature while moving. Once spinning a silk thread spewed from the right and left spinnerets located on the mouth of a larva breaks, the continuity is lost.

In this process, the direction in which a bagworm with the legs holding a rail moves, is the direction of movement of the bagworm in principle. As above-mentioned, a bagworm used in the present process is fixed at a position at which the legs of a bagworm are holding a rail. In this state, the bagworm cannot move in any direction other than the direction of movement. When a bagworm moves reverse on a rail, a ratchet equipped on the rail restricts such a reverse movement on the rail, and thus, the direction of movement inevitably results only in the direction of advance.

Another characteristic of the present process is that the rail is moved in the longitudinal direction automatically and/or by the movement of a bagworm. This makes it possible that a bagworm continuously spins on a rail even though fixed at given position.

The rail is moved by the movement impelling force of a bagworm moving with holding the rail with the legs. Accordingly, the direction of movement of the rail is opposite to the direction of movement of a bagworm. When the rail is a circular loop-shaped rail constituted around the marginal portion of a disc, the rail can move by rotating the disc by the movement of a bagworm. The rail may be moved automatically. In this case, the direction of movement of the rail is opposite to the direction of movement of a bagworm.

When the moving speed of a rail is based on the movement impelling force of a bagworm, it is substantially equal to the moving speed of the bagworm. Also when the rail is moved automatically, the moving speed of the rail is adjusted so as to be approximately equal to or less than the moving speed of a bagworm. When the rail is moved automatically, the rail can be moved using a known driving technique, for example, a combination of a motor and a gear. As above-mentioned, the usual moving speed of a bagworm is in the range of from 3 m/hr to 15 m/hr, or in the highest range of from 17 m/hr to 22 m/hr. Accordingly, when the rail is moved automatically, a speed (v) may be equal to or less than these speeds. For example, the moving speed is in the following ranges: $0 \text{ m/hr} < v \leq 22 \text{ m/hr}$, $0 \text{ m/hr} < v \leq 20 \text{ m/hr}$, $0 \text{ m/hr} < v \leq 17 \text{ m/hr}$, $0 \text{ m/hr} < v \leq 15 \text{ m/hr}$, $0 \text{ m/hr} < v \leq 12 \text{ m/hr}$, $0 \text{ m/hr} < v \leq 10 \text{ m/hr}$, $0 \text{ m/hr} < v \leq 8 \text{ m/hr}$, $0 \text{ m/hr} < v \leq 5 \text{ m/hr}$, $0 \text{ m/hr} < v \leq 4 \text{ m/hr}$, or $0 \text{ m/hr} < v \leq 3 \text{ m/hr}$.

Since a method according to the present invention enables a bagworm to continue to spin a silk thread on a rail, a long bagworm foothold silk thread can be produced.

3. Method of Producing Long Bagworm Silk Thread

3-1. Overview

A third aspect of the present invention is a method of producing a long bagworm silk thread. A production method according to the present invention makes it possible that a long bagworm foothold silk thread is produced from a bagworm in an efficient manner and in a large amount.

3-2. Method

Figure 9:
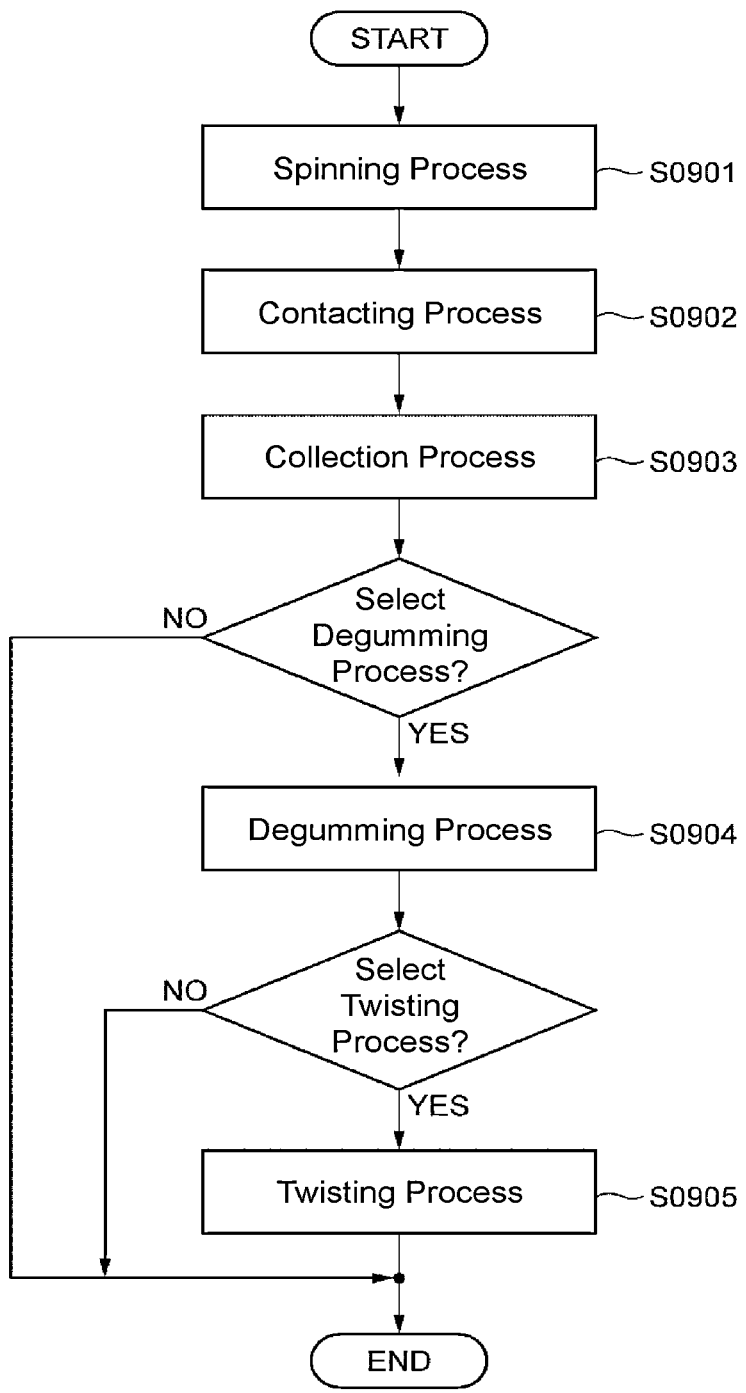
FIG. 9 is a basic process flow diagram of a method of producing a long bagworm silk thread according to the present invention.

A basic process flow of a production method according to the present invention is shown in FIG. 9. The production method according to the present invention comprises a spinning process (S0901), a contacting process (S0902), and a collection process (S0903) as essential production processes. The method also comprises a degumming process (S0904) and/or a twisting process (S0905) as optional processes. FIG. 4 illustrates a flow according to which the spinning process (S0901) is followed by the contacting process (S0902), but these essential processes can be performed concurrently. The optional processes are not limited to the basic flow. FIG. 9 illustrates a basic flow, wherein the collection process (S0903) is performed, followed by the degumming process (S0904) and the twisting process (S0905) in turns, but for example, as below-mentioned, the degumming process (S0904) may be performed concurrently as the contacting process (S0902), and the twisting process (S0905) may be performed after the collection process (S0903) and before the degumming process (S0904). Each of the processes will be specifically described below.

(1) Spinning Process (S0901)

The "spinning process" follows the spinning process in the method of producing a bagworm silk thread as described in the above-mentioned second aspect. Thus, a specific description of this process is omitted here. The spinning process in the present aspect is characterized by making a bagworm spin a long silk thread.

(2) Contacting Process (S0902)

The "contacting process" is a process of making a bagworm silk thread on a rail contact with a peeling solution and/or vapor. This process weakens the adhesive capability of a gummy material attaching the bagworm silk thread to the rail, thus making it easier to peel and collect the bagworm silk thread in the collection process. By performing this process immediately after a bagworm spins, it is possible to alleviate a physical burden on the bagworm silk thread on the rail and to peel the thread before the gummy material increases in adhesive strength while dried and solidified.

Figure 10:
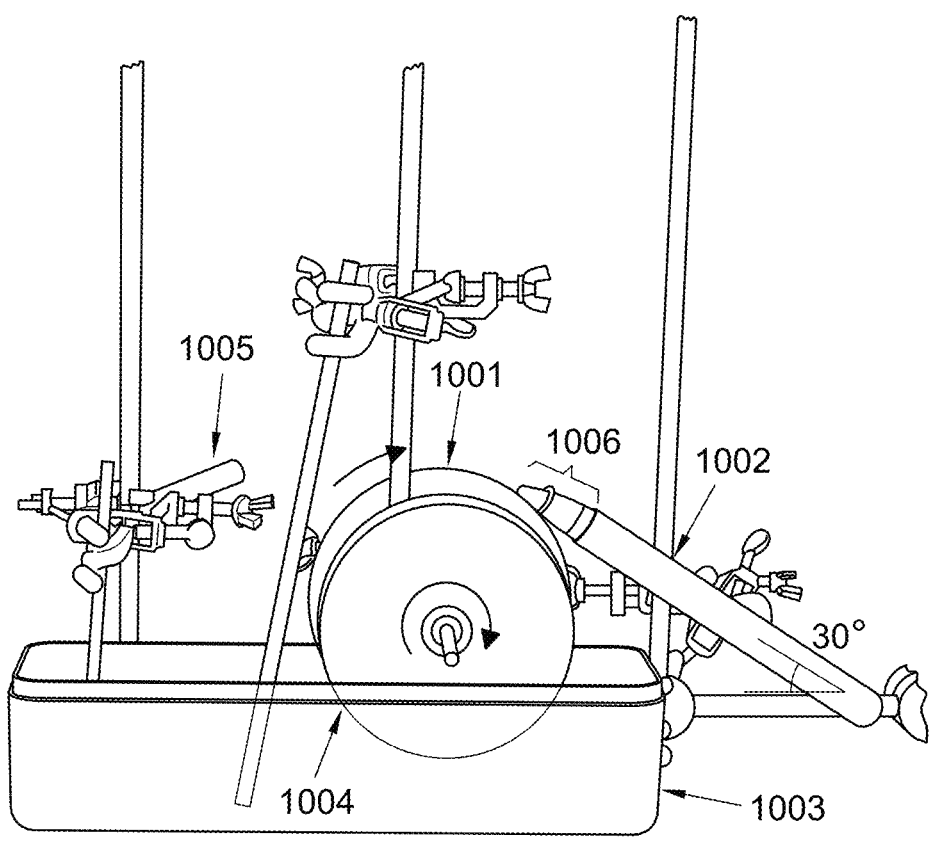
FIG. 10 is a view of an apparatus for producing a bagworm silk thread, manufactured in an Example in the present invention.

In this regard, this process is typically implemented after the spinning process (S0901), and may also be performed concurrently as the spinning process (S0901). For example, with such a thread-producing apparatus with a circular loop-shaped rail as shown in FIG. 2 or FIG. 10, the rail with a peeling solution attached thereto through soaking is rotated, resulting again in being a rail on which a bagworm spin. Because of this, the bagworm silk thread and the peeling solution on the rail come in contact with each other (the contacting process) concurrently as the bagworm spins (the spinning process). In this case, the rail is immersed in a peeling solution again after the spinning, and thus, the bagworm silk thread can be more easily peeled from the rail.

A peeling solution and vapor to be used in this process follows the peeling solution and vapor described in the first aspect.

A method of making a peeling solution of vapor contact with a bagworm silk thread attached to a rail in the spinning process is not limited. Examples of such methods comprise: a method in which the rail after the spinning process is immersed in a peeling solution in a tank; a method in which the rail after the spinning process is allowed to pass through water vapor filled into the chamber; a method in which a peeling solution is dripped onto a bagworm silk thread attached to the rail after the spinning process; a method in which water vapor is sprayed onto a bagworm silk thread attached to the rail after the spinning process; and combinations of these methods. That is, the same or different contacting processes can be performed a plurality of times during one cycle from the spinning process to the collection process.

Additionally, by using a degumming solution as a peeling solution the contacting process doubles as the degumming process (S0904) as described below. In this case, the subsequent collection process can collect a monofiber formed by separating a bifilament, not spun fiber. The degumming process will be described later.

(3) Collection Process (S0903)

The "collection process" is a process of peeling and collecting a bagworm silk thread attached to a rail after the contacting process. The bagworm silk thread after the contacting process is easier to peel from the rail because the adhesive capability of the gummy material is diminished. Accordingly, after the end of the bagworm silk thread is peeled from the rail using a peeling container or the like, and then, by adding tension to a direction different from the direction of movement of the rail, the bagworm silk thread can be easily peeled from the rail.

A method of collecting a bagworm silk thread peeled from the rail is not limited t as long as the method does not make the bagworm silk thread be torn. In a production method according to the present invention, a method in which a thread is reeled on a bobbin to be collected is preferable. A usual bobbin used in the art can be used. For example, the thread can be reeled around the periphery of a disc-shaped member, tubular member, plate-like member, or the like.

In a method of producing a bagworm silk thread according to the present invention, the rail is moved in a direction opposite to the direction of movement of a bagworm automatically and/or by a movement impelling force generated by the movement of the bagworm on the rail used in the spinning process. When this is done, the bagworm silk thread may be collected by rotating the bobbin synchronically with the movement of the rail. When the bobbin is synchronized with the movement of the rail, the rotation speed of the bobbin is substantially the same as the moving speed of the bagworm, that is, 3 m/hr to 15 m/hr, or in the highest range of 17 m/hr to 22 m/hr. Accordingly, the bobbin works at a speed equal to or less than the speed (v). For example, the working speed is in the following ranges: 0 m/hr<v≤22 m/hr, 0 m/hr<v≤20 m/hr, 0 m/hr<v≤17 m/hr, 0 m/hr<v≤15 m/hr, 0 m/hr<v≤12 m/hr, 0 m/hr<v≤10 m/hr, 0 m/hr<v≤8 m/hr, 0 m/hr<v≤5 m/hr, 0 m/hr<v≤4 m/hr, or 0 m/hr<v≤3 m/hr. When the bobbin is moved automatically, the rail can be moved using a known driving technique, for example, a combination of a motor and a gear.

The bobbin may be rotated in any direction. When the rail is a circular loop-shaped rail, a silk thread may be collected by rotating the bobbin in the same direction as the rotation direction of the rail or in another rotation direction. When the bobbin collects a bagworm silk thread in a rotation direction other than a direction opposite to the rotation direction of the rail, the thread reeling direction of the bagworm silk thread peeled from the rail needs to be changed. In this case, the bagworm silk thread withdrawn by peeling may be hooked on one or more reeling drums, pulleys, ring hooks, hooks, or the like, and then reeled around the bobbin. Examples of preferable embodiments comprise a method in which a circular loop-shaped rail and a bobbin are made coaxial and rotated in the same direction (a direction opposite to the direction of movement of a bagworm) automatically and/or by the movement impelling force of the bagworm, and then, the bagworm silk thread peeled from the rail is put on a ring hook or a reeling drum, and reeled around the bobbin in the same direction as the rotation direction of the rail. This method makes it possible that a bagworm silk thread spun on a rail is immediately collected in a relatively narrow space, and additionally, the bobbin is rotated concurrently as the rail automatically and/or by the movement impelling force of the bagworm. Thus, this method enables the spinning and the collection to be performed concurrently, and accordingly, is efficient. Additionally, the bagworm silk thread is peeled from the rail before the gummy material secreted concurrently as the spinning of the bagworm silk thread is dried and solidified, and thus, a weak force enables the thread to be easily collected without giving no physical damage. This process makes it possible to obtain a long bagworm foothold silk thread.

(4) Degumming Process (S0904)

The "degumming process" is a process of degumming a long bagworm silk thread. The term "degumming" refers to removing a sericin-like gummy material from a spun fiber to obtain a monofiber. This process is typically performed after the above-mentioned collection process, and may be performed concurrently as the contacting process, as above-mentioned. Additionally, when the twisting process is performed before this process and after the collection process, as described below, this process may be performed after the twisting process. This process is an optional process and may be performed if necessary.

A method of degumming a bagworm silk thread is not limited as long as a gummy material can be removed without weakening the strength of a fiber component of the silk thread. For example, a method of degumming a silkworm silk thread may be applied. Specifically, a bagworm silk thread collected in the collection process is immersed in a solution having a sodium bicarbonate concentration of 0.01 mol/L to 0.1 mol/L, 0.03 mol/L to 0.08 mol/L, or 0.04 mol/L to 0.06 mol/L. More preferably, the thread is boiled for a time period from 5 minutes to 1 hour, 10 to 40 minutes, or 15 to 30 minutes. This process makes it possible to obtain a monofiber from a long foothold silk thread.

(5) Twisting Process (S0905)

The "twisting process" is a process of twisting a bagworm silk thread obtained after the collection process or the degumming process. The term "twisting" refers to winding threads together to produce a yarn. In this process, plural bagworm silk spun fibers and/or monofibers are twisted to produce bagworm silk yarns having toughness.

In the twisting process, monofibers from bagworm silk threads obtained after the degumming process may be gathered into a bundle and then twisted, or alternatively bagworm silk spun fibers obtained after the collection process may be gathered into a bundle and then twisted. In the former case, a twisted bagworm silk yarn without a gummy material is obtained. In the latter case, a twisted bagworm silk yarn consisting of spun fibers containing a gummy material is obtained. Thus, the obtained bagworm silk yarn may be used as a bagworm silk yarn which has not undergone the degumming process and consequently contains a gummy material, or may be degummed as necessary to produce a twisted bagworm silk yarn from without a gummy material.

In this process, a bagworm silk thread may be blended with another fiber, for example, an animal fiber such as a silkworm silk thread, a plant fiber such as a cotton fiber, a synthetic fiber such as a polyester fiber, or a recycled fiber such as rayon, or the like, to form a bundle of fibers, which is in turn twisted. In the production of one strand of twisted bagworm silk yarn, the number of constituent spun fibers and/or monofibers is not limited to a particular number. For example, the number ranges from 2 to 200, from 4 to 150, from 6 to 100, from 8 to 50, or from 10 to 30.

The twisting is not limited to any particular method. Any twisting method known in the art may be implemented. Examples of the methods include right-laid (S-laid) and left-laid (Z-laid). The twist number may be determined as appropriate. Plural strands of twisted bagworm silk yarn may be further twisted together by a process called plying to produce a thicker bagworm silk yarn. The twisting operation may be performed by hand or by using a yarn twister.

Long bagworm silk thread, which is obtained by a production method according to the present invention, can be spun together into a longer bagworm silk yarn.

A long bagworm silk thread, which has hitherto been considered impossible to produce, can be produced as a monofiber or a fiber assembly thorough the above-mentioned processes. Accordingly, a fabric comprising a bagworm foothold silk thread, which has hitherto been impossible to produce, can also be produced using a long bagworm silk thread according to the present invention as a sole material or in combination with another fiber. A fabric made of a bagworm silk thread is beautiful and smooth, has excellent tensile strength. Thus, a long bagworm silk thread is promising not only as a material for clothes but also as a special material for, for example, medical materials and protective clothes, as in the case of a spider thread. The Long bagworm silk thread can further be used for quality fabric products, for example, quality legless chairs, sofas, curtains, fabric wallpapers, and the like, to which strong friction force is often applied.

EXAMPLES

<Fabrication of Apparatus for Producing Bagworm Silk Thread, and Verification of Length of Produced Thread>
(Purpose)

An apparatus for producing a bagworm silk thread according to the present invention was fabricated, and whether or not the length of a bagworm foothold silk thread which could be automatically produced by the apparatus was 1 m or more was verified.
(Method)

1. Fabrication of Apparatus

In this Example, an apparatus for producing a bagworm silk thread as described in the first aspect of the present invention was fabricated. The actual thread-producing device is shown in FIG. 10.

The movable rail (1001) was a circular loop-shaped rail constituted around the periphery of a disc having a diameter of 12 cm and a thickness of 2.1 mm. This disc can be rotated around the central axis of the circle in the direction (clockwise) shown in the figure.

A polypropylene-made centrifuge tube having a diameter of 18 mm (having an inner diameter of 16 mm) was used for the fixator (1002); this centrifuge tube was slanted at an angle of approximately 30 degrees with respect to the horizontal plane; and the legs of a bagworm fixed to the fixator were allowed to hold the upper portion of the movable rail.

A storage tank storing 1 L of a peeling solution of 0.1% polyethylene glycol stearate (n=approximately 40, from Tokyo Chemical Industry Co., Ltd., Cas. No. 9004-99-3) was used as a peeling container (1003). The movable rail was placed vertically in the apparatus, and the lower ¼ portion of the disc was immersed in the peeling solution in the storage tank.

The collection device (1004) was a disc having a diameter of 12 cm and a thickness of 16 mm, and was enabled to be rotated coaxially with the movable rail. This structure made it possible that the movable rail and the collection device synchronized with each other and were rotated in the same direction (clockwise).

Additionally, an S-shaped hook made of stainless steel wire having a diameter of 0.3 mm was located as the thread hook (1005) between the movable rail and the collection device. The bagworm silk thread passed through the peeling container was hooked on this S-shaped hook, introduced through the upper portion of the wind-up portion placed on the periphery of the collection device, and fixed. Via a thread hook, the bagworm silk thread can be reeled in the same direction even if the movable rail and the collection device are rotated in the same rotation direction. The tension of wind-up by the collection device is transferred to the bagworm silk thread which is on the movable rail and has passed through the peeling container via the thread hook, and this force makes the bagworm silk thread be peeled from the movable rail. Accordingly, it is possible that, after the bagworm is fixed to the fixator, and the legs hold the movable rail, the peeling and the collection are implemented automatically until the bagworm stops the spinning action, that is, moving.

2. Production of Long Bagworm Silk Thread (1) Material

As bagworms, the last instar larvae of *Eumeta japonica* collected in Ibaraki, Japan, were used (n=10).
(2) Method of Producing Thread The above-mentioned bagworm (1006) in a nest was fixed to the fixator. Half of the nest of the bagworm was inserted into the centrifuge tube, and Parafilm (registered trademark) was wound around the boundary between the nest and the centrifuge tube to fix the nest. The legs of the bagworm were allowed to hold the movable rail. The time from the point of time at which the bagworm started moving forward and spinning to the point of time at which the continuous spinning stopped was measured as a thread-producing time. The length of the produced bagworm silk thread which could be collected in the collection device during the time was measured. Additionally, the per-hour spinning speed of the bagworm was calculated from the thread-producing time and the length of the produced thread. The same thread-producing method was performed on 10 bagworms.
(Results)

The thread-producing time, the length of the spun thread, and the spinning speed calculated therefrom are tabulated in Table 1.

TABLE 1

| # | Thread-producing Time (min) | Length of Produced Thread (m) | Spinning Speed (m/hr) |
|---|---|---|---|
| 1 | 140 | 28.8 | 12.3 |
| 2 | 165 | 22.0 | 8.0 |
| 3 | 240 | 17.2 | 4.3 |
| 4 | 165 | 16.8 | 6.1 |
| 5 | 60 | 7.2 | 7.2 |
| 6 | 90 | 19.3 | 12.9 |
| 7 | 240 | 19.9 | 5.0 |
| 8 | 225 | 33.9 | 9.0 |
| 9 | 205 | 34.2 | 10.0 |
| 10 | 55 | 11.0 | 12.0 |
| Ave. | 158.5 | 21.0 | 8.7 |

The above-mentioned results have revealed that an apparatus for producing a bagworm silk thread, used as an embodiment of a method of producing a long bagworm according to the invention, makes it possible that a continuous bagworm silk thread approximately 7 m as the shortest thread or as long as 20 m on the average is automatically produced, although such a thread is conventionally difficult to produce even by 1 m.

All publications, patents, and patent applications cited herein should be incorporated herein by reference in their entirety.

The invention claimed is:

1. A method of producing a bagworm silk thread from a bagworm, comprising
   a spinning process of making the bagworm hold a rail with its legs and continuously spin along the rail, wherein
   the rail has a width smaller than a maximum width between right and left legs of the bagworm for use, and is configured to be able to be held by the legs of the bagworm, and
   in the spinning process, the bagworm separated from a nest or a nest containing the bagworm is fixed at a position such that the legs of each bagworm can hold the rail,
   wherein the rail is configured to be moved in a longitudinal direction of the rail automatically and/or by a movement impelling force of the bagworm legs.

2. A method of producing a long bagworm silk thread, comprising:
   a spinning process of making a bagworm or the bagworm having a nest hold a rail with its legs and continuously spin along the rail, wherein
   the rail has a width smaller than a maximum width between right and left legs of the bagworm used for thread production, and is configured such that the legs of the bagworm can hold the rail;
   a contacting process of bringing a bagworm silk thread on the rail in contact with a peeling solution and/or vapor; and
   a collection process of peeling the bagworm silk thread from the rail after the contacting process to collect the bagworm silk thread,
   wherein in the spinning process, the bagworm separated from a nest or a nest containing the bagworm is fixed at a position such that the legs of the bagworm can hold the rail,
   wherein the rail is configured to be moved in a longitudinal direction of the rail automatically and/or by a movement impelling force of the bagworm legs.

3. The method according to claim 2, further comprising a degumming process of degumming the bagworm silk thread during the contacting process, during the collection process, and/or after the collection process.

4. The method according to claim 2, further comprising a twisting process of twisting the bagworm silk thread after the collection process and/or after the degumming process.

5. The method according to claim 1, wherein the rail is loop-shaped.

* * * * *